(12) United States Patent
Xu et al.

(10) Patent No.: US 11,634,759 B2
(45) Date of Patent: Apr. 25, 2023

(54) REAL-TIME FLUORESCENCE QUANTITATIVE PCR DETECTION METHOD AND KIT BASED ON METAL RUTHENIUM COMPLEX

(71) Applicant: SHAANXI UNIVERSITY OF SCIENCE & TECHNOLOGY, Shaanxi (CN)

(72) Inventors: Qinfeng Xu, Shaanxi (CN); Jing Dong, Shaanxi (CN); Hongxin Song, Shaanxi (CN); Jianlan Liu, Shaanxi (CN)

(73) Assignee: SHAANXI UNIVERSITY OF SCIENCE & TECHNOLOGY, Shaanxi (CN)

( * ) Notice: Subject to any disclaimer, the term of this patent is extended or adjusted under 35 U.S.C. 154(b) by 48 days.

(21) Appl. No.: 17/056,017

(22) PCT Filed: Jun. 21, 2019

(86) PCT No.: PCT/CN2019/092406
§ 371 (c)(1),
(2) Date: Nov. 17, 2020

(87) PCT Pub. No.: WO2019/242767
PCT Pub. Date: Dec. 26, 2019

(65) Prior Publication Data
US 2021/0348223 A1     Nov. 11, 2021

(30) Foreign Application Priority Data
Jun. 22, 2018   (CN) .......................... 201810653529.1

(51) Int. Cl.
*C12Q 1/68*     (2018.01)
*C12Q 1/6851*   (2018.01)
*C12Q 1/686*    (2018.01)

(52) U.S. Cl.
CPC ........... *C12Q 1/6851* (2013.01); *C12Q 1/686* (2013.01)

(58) Field of Classification Search
None
See application file for complete search history.

(56) References Cited

FOREIGN PATENT DOCUMENTS

| CN | 101522909 A | * | 9/2009 | ............... B01L 3/508 |
|----|-------------|---|--------|---------------------------|
| CN | 101696451 A |   | 4/2010 |                           |
| CN | 101914631 A |   | 12/2010 |                          |
| CN | 101928784 A |   | 12/2010 |                          |
| CN | 102220417 A |   | 10/2011 |                          |
| CN | 108753933 A |   | 11/2018 |                          |

OTHER PUBLICATIONS

Ahmed et al. (Analyst 2013, 138, 907-915) (Year: 2013).*
Defever et al. Anal Chem, 2011, 83:1815-1821, IDS reference) (Year: 2011).*
Gao et al. (J of Inorg Chem, 2006, 100:1487-1494) (Year: 2006).*
Martin et al. (ACS Sens, 2016, 1,904-912) (Year: 2016).*
Xu et al. (Anal Chem, 2019, 91:8777-8782) (Year: 2019).*
Defever et al. (J Am Chem Soc, 2009, 131, 11433-11441) (Year: 2009).*
Lian-Sheng Ling et.al. "A Novel Method toDetermine DNA byUse of Molecular"Light Switch" ofRu(phen)2(dppz)2+". Microchemical Journal, vol. 63, No. 3, Nov. 30, 1999 (Nov. 30, 1999), pp. 356-364, entire document.
Guanying Li et.al. "Ruthenium(ii) complexes with dppz: from molecular photoswitch to biological applications". Dalton Transactions, Jul. 31, 2016 (Jul. 31, 2016), pp. 13261-13276, entire document.
CN search report re: Application No. 201810653529.1.
Defever, T. et al. "Real-Time Electrochemical PCR with a DNA Intercalating Redox Probe". Anal Chem., vol. 83, No. 5, Mar. 1, 2011 (Mar. 1, 2011), pp. 1815-1821, entire document.

* cited by examiner

*Primary Examiner* — Stephanie K Mummert
(74) *Attorney, Agent, or Firm* — Gang Yu

(57) ABSTRACT

The present disclosure discloses a real-time fluorescence quantitative polymerase chain reaction (PCR) detection method and kit based on a metal ruthenium complex. The present disclosure is capable of establishing the detection method for performing a real-time fluorescence quantitative PCR by using the metal ruthenium complex as fluorescence dye.

8 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: pre-primer (5'-3')
<220> FEATURE:
<221> NAME/KEY: misc_feature
<222> LOCATION: (1)..(22)

<400> SEQUENCE: 1
tttaacagct aaagagtttg gt                                              22

<210> SEQ ID NO 2
<211> LENGTH: 22
<212> TYPE: DNA
<213> ORGANISM: Artificial Sequence
<220> FEATURE:
<223> OTHER INFORMATION: post-primer (5'-3')
<220> FEATURE:
<221> NAME/KEY: misc_feature
<222> LOCATION: (1)..(22)

<400> SEQUENCE: 2
ttttcataat cratcactgg ac                                              22

<210> SEQ ID NO 3
<211> LENGTH: 19
<212> TYPE: DNA
<213> ORGANISM: Artificial Sequence
<220> FEATURE:
<223> OTHER INFORMATION: pre-primer (5'-3')-2
<220> FEATURE:
<221> NAME/KEY: misc_feature
<222> LOCATION: (1)..(19)

<400> SEQUENCE: 3
tccgcaggag ttgaagagg                                                  19

<210> SEQ ID NO 4
<211> LENGTH: 19
<212> TYPE: DNA
<213> ORGANISM: Artificial Sequence
<220> FEATURE:
<223> OTHER INFORMATION: post-primer (5'-3')-2
<220> FEATURE:
<221> NAME/KEY: misc_feature
<222> LOCATION: (1)..(19)

<400> SEQUENCE: 4
cagcagcgtg tctgtttca                                                  19
```

US 11,634,759 B2

REAL-TIME FLUORESCENCE QUANTITATIVE PCR DETECTION METHOD AND KIT BASED ON METAL RUTHENIUM COMPLEX

TECHNICAL FIELD

The present disclosure relates to a polymerase chain reaction (PCR) detection method and an application thereof, and in particular to applying a metal ruthenium complex to a nucleic acid amplification detection system, such as a detection method for a real-time fluorescence quantitative PCR (qPCR).

BACKGROUND

Nucleic acid amplification detection has very important significance to the fields of environment detection and food quality and safety and the like. A polymerase chain reaction (PCR) generates a large number of specific nucleic acid sequences through in-vitro amplification, and has been widely applied to molecular biology detection. The traditional polymerase chain reaction often requires electrophoresis to verify an amplification product, it is time-consuming and laborious, the initial template concentration can not be quantified, and it is easy to cause amplicon contamination. In order to overcome the defects of electrophoresis endpoint detection, a real-time fluorescence quantitative PCR technology is developed, a corresponding fluorescence signal is generated by each PCR cycle, and a standard curve is obtained by analyzing a cycle threshold of a known standard substance, so accurate calculation can be achieved to the nucleic acid concentration in an unknown sample.

The real-time fluorescence quantitative PCR is mainly divided into a DNA-binding dye method and a probe method. The probe method has strong specificity and does not require PCR post-processing, but a probe needs to be synthesized according to a specific sequence, and the cost is relatively higher; and fluorescence DNA-binding dye hardly fluoresces in solution, it fluoresces strongly when bound to a DNA, and is proportional to the total amount of the DNA produced by the PCR. The DNA-binding dye is bound to a DNA double-strand with a non-sequence specificity, so the probe does not need to be synthesized according to the specific sequence, and the cost is relatively low, but a non-specific amplification product can also generate a fluorescence signal, the specificity of the PCR amplification product needs to be identified by measuring a melting curve of the amplification product.

At present, the commercially available dyes in the real-time fluorescence quantitative PCR, such as SYBR Green I and Eva Green, are commercial reagents with higher cost. In addition, the most widely used SYBR Green I has problems, such as the greater inhibition is produced to the reaction and a signal to noise ratio is lower, in an amplification process, in application, it is also discovered that the SYBR Green I has a phenomenon of the poorer stability in high temperature and light source excitation. Therefore, it is necessary to develop new-type fluorescence dye, which is economical and environment-friendly, good in photostability, and robust in practicability, for use in nucleic acid detection and portable kits.

It is reported that inorganic metal ruthenium complexes with nucleic acid molecule "light switch" behavior, such as a ruthenium polypyridine complex ([Ru(phen)$_2$(dppz)]$^{2+}$, [Ru(bpy)$_2$(dppz)]$^{2+}$, dppz=dipyrido[3,2-a:2',3'-c]phenazine, bpy=2,2'-bipyridine,phen=1,10-phenanthroline) can be used in the highly sensitive detection of nucleic acid, and also has some characters superior to other organic binding dye, such as low fluorescence background, strong water solubility, and large stoke's shift (see references for details: J. Am. Chem. Soc. 1990, 112, 4960; Microchemical Journal 1999, 63, 356; Microchimica Acta 2000, 134, 57; Analytica Chimica Acta 2000, 403, 209; AnalyticaChimica Acta 2001, 436, 207; Dalton Transactions 2016, 45, 13261). It is indicated from other research that the ruthenium metal complex can be used in gel electrophoresis to analyze the fluorescence dye of the PCR amplification product (Method Enzymol. 1993, 226, 576). However, in the field of real-time PCR analysis, research and report on application thereof are not seen yet now, reasons include: 1) at present, the research of the metal ruthenium complex is mainly concentrated in the field of bio-inorganic chemistry, and a PCR reaction system has own characteristics itself, the background of molecular biology is also required for performing the real-time PCR amplification research, which belongs to the field of interdisciplinary research; and 2) due to special fluorescence properties of the metal ruthenium complexes, their fluorescence signals can not be high-sensitively detected by all of real-time PCR meters in the market, and the requirements of hardware limit researchers to research on the application of the metal ruthenium complex in the PCR analysis field in a certain degree.

SUMMARY

A purpose of the present disclosure is to provide a real-time fluorescence quantitative PCR detection method and a kit based on a metal ruthenium complex.

In order to achieve the above purpose, the present disclosure adopts the following technical scheme.

One purpose of the present disclosure is to provide a real-time fluorescence quantitative PCR detection method based on a metal ruthenium complex, including the following steps.

The metal ruthenium complex is used as a dye component in a real-time fluorescence quantitative PCR reaction system; multiple nucleic acid samples with different copy numbers are used as standard substances, each standard substance is respectively used as an amplification template component in the real-time fluorescence quantitative PCR reaction system, and a real-time fluorescence quantitative PCR is respectively performed according to a preset reaction program, when reaction is over, a standard curve is drawn according to a cycle threshold (Ct value) of each standard substance; a nucleic acid sample with an unknown copy number is used as an amplification template component in the real-time fluorescence quantitative PCR reaction system, the real-time fluorescence quantitative PCR is performed according to the reaction program, and a DNA copy number of the sample is calculated according to the standard curve and a cycle threshold of the nucleic acid sample with the unknown copy number.

Preferably, a final concentration of the metal ruthenium complex in the real-time fluorescence quantitative PCR reaction system is 0.5-10 μM. A final volume of the reaction system is 10-20 μL.

Preferably, the metal ruthenium complex is selected from one of ruthenium polypyridine complexes, such as [Ru(phen)$_2$(dppz)]$^{2+}$, and [Ru(bpy)$_2$(dppz)]$^{2+}$ and so on. In order to enhance a qPCR analysis performance, it may be selected from one of other metal ruthenium complexes with nucleic acid molecule light switch behavior which are obtained by performing further structure modification on ligands, such as phen, bpy and dppz, of the ruthenium polypyridine complex.

Preferably, an extending phase of the real-time fluorescence quantitative PCR collects a signal by using a certain fluorescence channel, the optimal fluorescence excitation wavelength and emission wavelength of the fluorescence channel are 400-500 nm and 550-750 nm respectively, the cycle threshold of the standard substance or the nucleic acid sample with the unknown copy number is obtained according to the signal.

Preferably, if the nucleic acid sample is a RNA, before amplification, the extracted RNA is reverse-transcribed into a DNA.

Preferably, the real-time fluorescence quantitative PCR detection method specifically includes the following steps.

1) Design of Primer

According to different detection purposes and samples, a target sequence is selected and a primer is designed;

2) Preparation of Reaction System

A thermostable DNA polymerase, the primer, dNTP, reaction buffer, a template DNA and the above metal ruthenium complex and the like are added to a PCR reaction tube, and water is added to make up until the final volume;

3) Real-Time Fluorescence Quantitative PCR

According to the different target sequences and primers, a amplification program is determined; a DNA sample with a known initial concentration is used as a template, after initial denaturation is performed on the template, a circular reaction is executed according to the amplification program and signal collection is performed in an extending step of a circular reaction, a collection channel of the fluorescence signal is: 400-500 nm of an excitation wavelength, and 550-750 nm of an emission wavelength; after the circular reaction is over, extending is performed again; and then according to the collected signal, an amplification curve is established, and a cycle threshold of the DNA sample is determined by the amplification curve;

4) The step 3) is repeated, the cycle threshold of each DNA sample with the different initial concentrations is obtained, and a standard curve is established in combination with the concentration of the corresponding DNA sample; and 5) According to the step 3), a DNA sample with an unknown initial concentration is amplified, to obtain a corresponding cycle threshold and it is substituted into the standard curve obtained in the step 4), thereby an initial concentration of the DNA sample is obtained by calculating.

Preferably, the amplification program is as follows: performing heat-denaturation on the template after the initial denaturation, renaturing a primer with a single-strand template obtained by thermal denaturation, then extending under the effect of the DNA polymerase.

Preferably, the DNA sample with the unknown initial concentration is obtained by extraction and purification through a kit method.

Another purpose of the present disclosure is to provide a real-time fluorescence quantitative PCR detection kit based on a metal ruthenium complex, the kit includes the above metal ruthenium complex, a thermostable DNA polymerase, 4 nucleotides (dNTP) and a metal ion mixture.

The benefit effect of the present disclosure is as follows.

The present disclosure achieve the real-time amplification and quantitative detection to the nucleic acid, through enabling the metal ruthenium complex to be combined with a real-time fluorescence quantitative PCR technology, and using a character that fluorescence intensity is greatly improved while the metal ruthenium complex as the fluorescence dye is combined with a nucleic acid (such as, dsDNA). The present disclosure use the inorganic metal ruthenium complex which is the nucleic acid molecule light switch as the fluorescence dye, has the advantages of easy synthesis, stable structure, good water solubility and the like, and is widely used in nucleic acid quantification of various samples. Therefore, it can replace existing commercial organic dyes, and be served as new-type and promising DNA-binding dye applied to the real-time fluorescence quantitative PCR detection, it has the important significance to develop a nucleic acid detection reagent.

DETAILED DESCRIPTION OF THE EMBODIMENTS

The present disclosure is further described in detail below in combination with the drawings and embodiments, the embodiments are only used to explain the present disclosure, rather than to limit the present disclosure.

(I) Feasibility of Metal Ruthenium Complex Served as Fluorescence Dye in Real-Time Fluorescence Quantitative PCR A conserved sequence of a *Staphylococcus aureus* fem gene was used as an amplified target sequence, a design of an amplification primer was completed in August 2017, and the amplification primer was synthesized and purified by Sangon Biotech (Shanghai) Co., Ltd A specific sequence is as follows:

```
pre-primer (5'-3'):
TTTAACAGCTAAAGAGTTTGGT;
and post-primer (5'-3'):
TTTTCATAATCRATCACTGGAC.
```

Figure 1A:
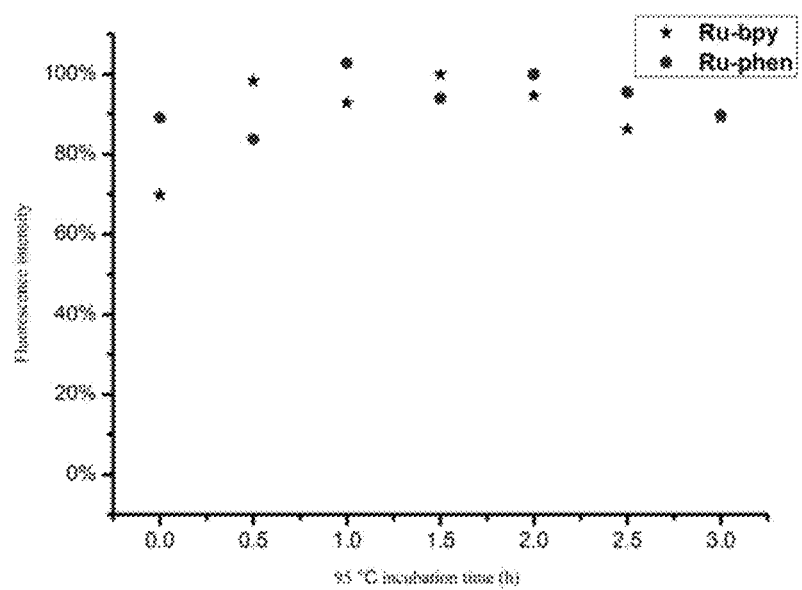
FIG. 1A is the stability of a fluorescence signal while a metal ruthenium complex is incubated in 95° C., herein Ru-bpy represents $[Ru(bpy)_2(dppz)]^{2+}$ and Ru-phen represents $[Ru(phen)_2(dppz)]^{2+}$.

1. Fluorescence Signal Stability of Metal Ruthenium Complex Incubated in High Temperature Metal ruthenium complexes $[Ru(bpy)_2(dppz)]^{2+}$ and $[Ru(phen)_2(dppz)]^{2+}$ were respectively incubated in a high temperature of 95° C. in Tirs buffer solution with pH 8.0, fluorescence intensity signal detection was performed every a certain time (for example, 0.5 h), a result was as shown in FIG. 1A, a fluorescence signal was only fluctuated within a small range during 3 hours, and there was no apparent drop, it was indicated that the metal ruthenium complex might keep the fluorescence intensity stable in a PCR alkaline amplification condition and a high temperature denaturation step.

2. Real-Time Fluorescence Quantitative PCR Amplification

1) Bacteria culture amplification and DNA extraction: after an LB culture medium was used to perform bacteria enrichment treatment, a kit is used to extract a genomic DNA.

2) Establishment of qPCR reaction system: a reaction system is 10 μL, herein a DNA template extracted in the previous step was 1.0 μL (200 ng/μL), 2×Taq PCR Mastermix was 5.0 μL, each of the forward primer and reverse primer was 1.0 μL (4 μM), 20 μM of the metal ruthenium complex $[Ru(bpy)_2(dppz)]^{2+}$ was 1.5 μL, water has been used to make up the final volume of the sample, and NTC (no template control) was performed.

3) Three-step PCR reaction program used by qPCR: 95° C. of initial denaturation was performed for 5 min; 95° C. of denaturation was performed for 15 s, 57° C. of annealing was performed for 15 s, 68° C. of extending was performed for 30 s and a fluorescence signal was collected, ranges of excitation and emission wavelengths of a signal channel are 400-500 nm and 550-750 nm respectively, it was 30 cycles in total; and 68° C. of the extending was performed again for 5 min. A melting curve was in 60-95° C., and the signal was measured once every 0.5° C., a initial temperature increasing rate was 5° C. Is.

Figure 1B:
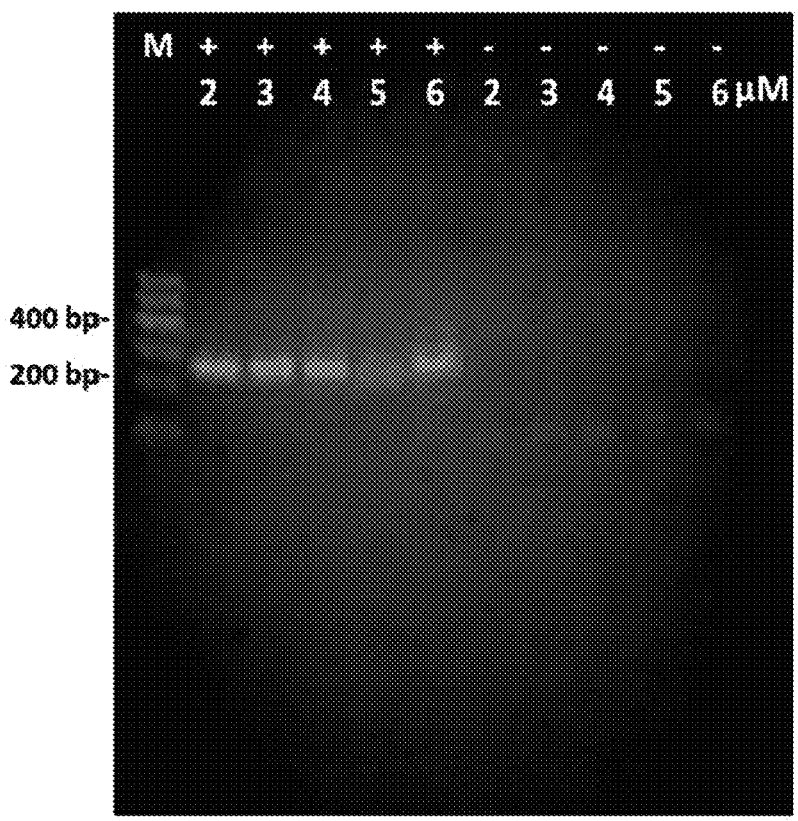
FIG. 1B is an inhibitory electrophoresis diagram of a PCR amplification reaction while the $[Ru(bpy)_2(dppz)]^{2+}$ is served as fluorescence dye, herein + represents an experiment group, and − resents a blank group.
Figure 1C:
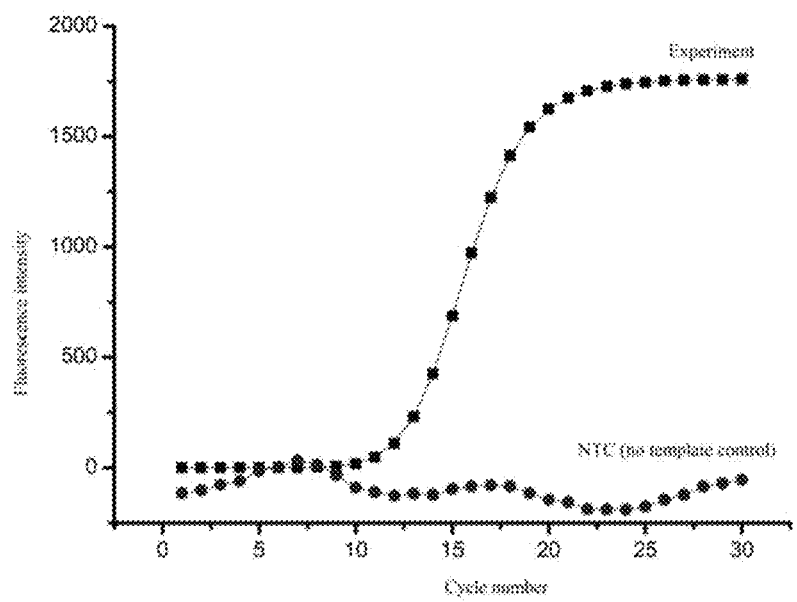
FIG. 1C is an amplification curve diagram while the $[Ru(bpy)_2(dppz)]^{2+}$ is served as the dye.
Figure 1D:
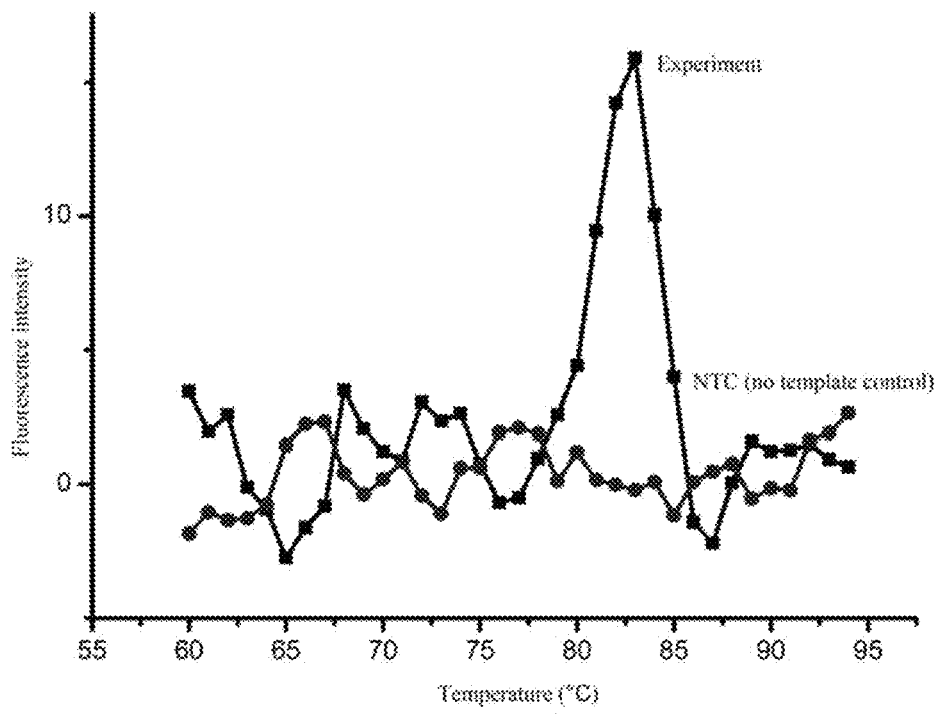
FIG. 1D is a melting curve diagram while the $[Ru(bpy)_2(dppz)]^{2+}$ is served as the dye.

4) Experiment Result:

The extracted DNA was used as a template, a specific primer was added, and a real-time fluorescence quantitative PCR amplification experiment was performed, to obtain the amplification curve as shown in FIG. 1C and a characteristic melting peak of the amplification sequence as shown in FIG. 1D, and the length of product was verified by agarose gel electrophoresis so the feasibility of the metal ruthenium complex served as the fluorescence dye in the real-time fluorescence quantitative PCR was proved.

Figure 1E:
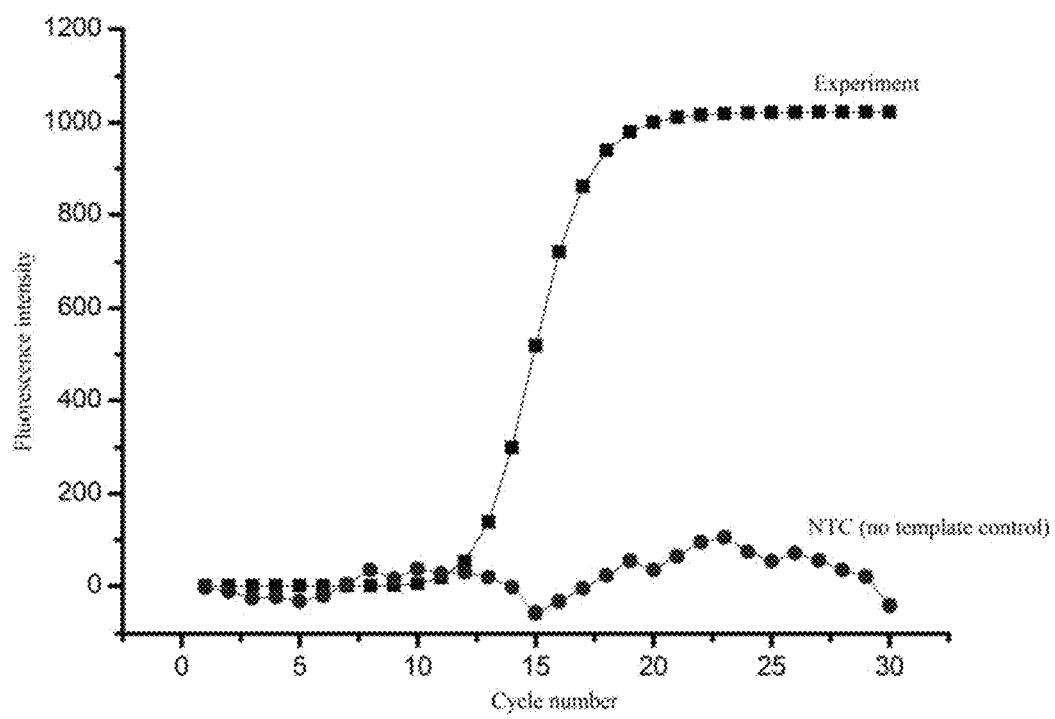
FIG. 1E is an amplification curve diagram while the $[Ru(phen)_2(dppz)]^{2+}$ is served as the dye.
Figure 1F:
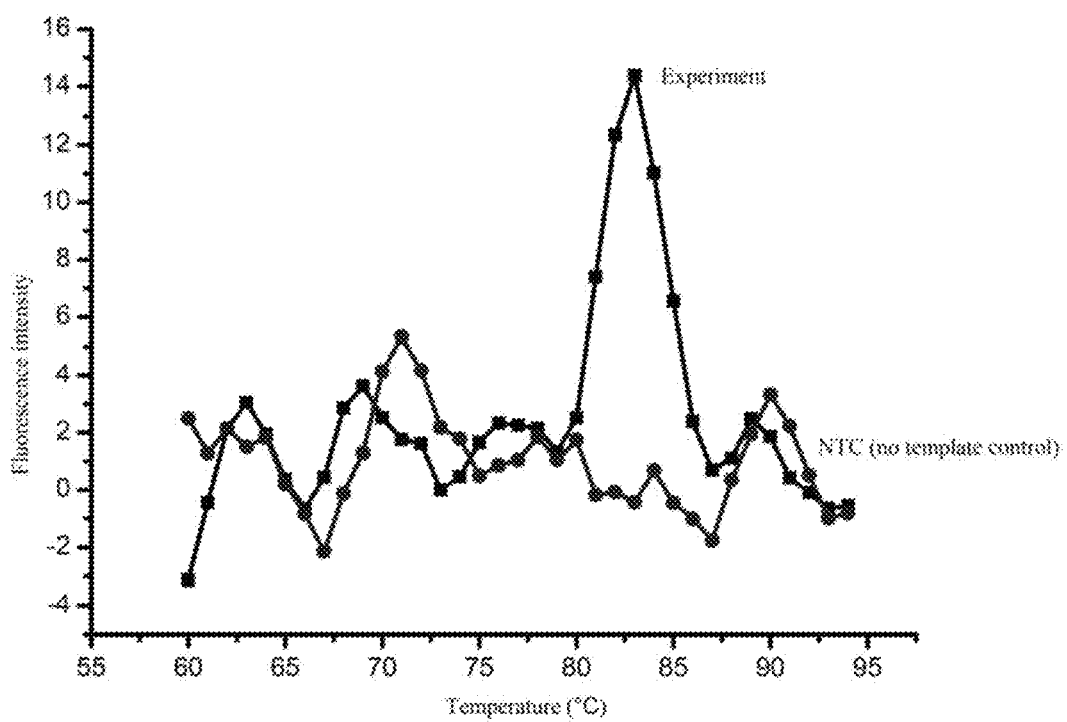
FIG. 1F is a melting curve diagram while the $[Ru(phen)_2(dppz)]^{2+}$ is served as the dye.

The real-time fluorescence quantitative PCR amplification was performed on another metal ruthenium complex $[Ru(phen)_2(dppz)]^{2+}$ by using the same method, to obtain the amplification curve and the melting curve as shown in FIG. 1E and FIG. 1F, it had the same performance as using the $[Ru(bpy)_2(dppz)]^{2+}$.

3. Inhibitory Effect of Dye Concentration on PCR Reaction the metal ruthenium complex $[Ru(bpy)_2(dppz)]^{2+}$ with different final concentrations (2, 3, 4, 5, and 6 μM) was added to the PCR reaction system for the amplification, 2% agarose-gel electrophoresis detection was performed, and the NTC was performed, a result was as shown in FIG. 1B, an experiment group (+, amplification target sequence) had bands of amplification products at all concentrations, it was indicated that the metal ruthenium complex had almost no inhibitory effect on the PCR amplification within a certain concentration range (1-10 μM), and could be suitable for the real-time fluorescence quantitative PCR, but the apparent inhibition would occur if it exceeded this range. It could be observed from a blank group (−, no template control) that targeted amplification fragments were not found, so it is indicated that cross-contamination did not occur. A volume of the typical reaction system was 10-20 μL.

(II) Linear Range and Sensitivity Analysis of Real-Time Fluorescence Quantitative PCR by Using Metal Ruthenium Complex $[Ru(Bpy)_2(Dppz)]^{2+}$ 1) Bacteria culture and template DNA extraction were the same as (I).

2) Primer synthesis was the same as (I).

3) Template DNA stock solution ($1\times10^7$ copies/μL) was diluted into $1\times10^6$ copies/μL, $1\times10^5$ copies/μL, $1\times10^4$ copies/μL, $1\times10^3$ copies/μL, $1\times10^2$ copies/μL and $1\times10^1$ copies/μL in 10 times of a gradient.

4) A qPCR reaction system was the same as (I).

5) A qPCR reaction program was the same as (I).

Figure 2A:
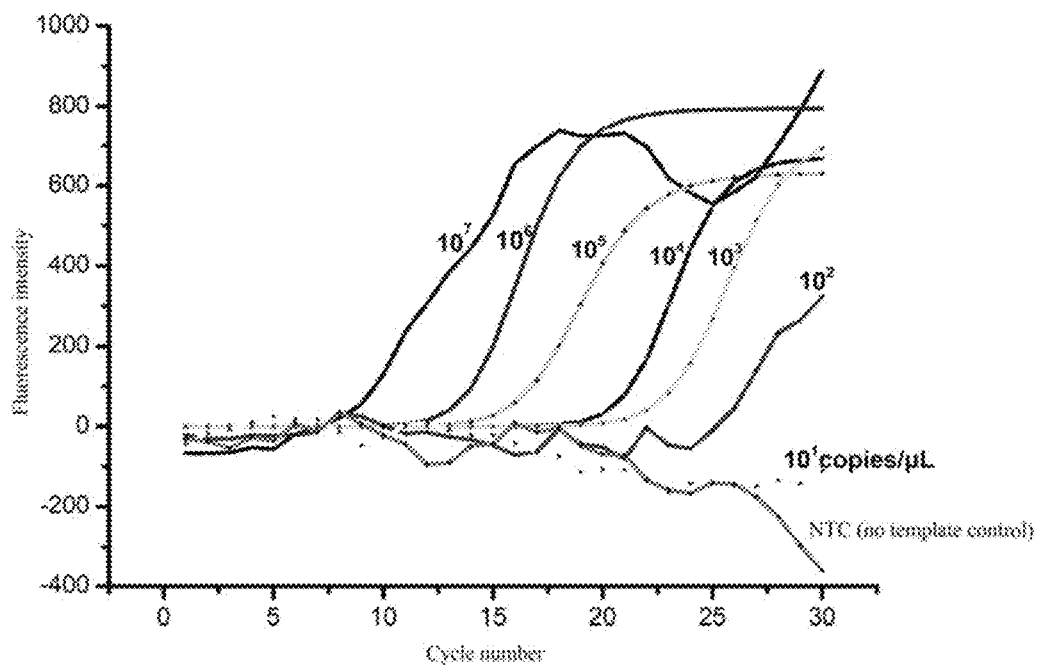
FIG. 2A is a template concentration gradient amplification curve diagram while the $[Ru(bpy)_2(dppz)]^{2+}$ is served as the dye.
Figure 2B:
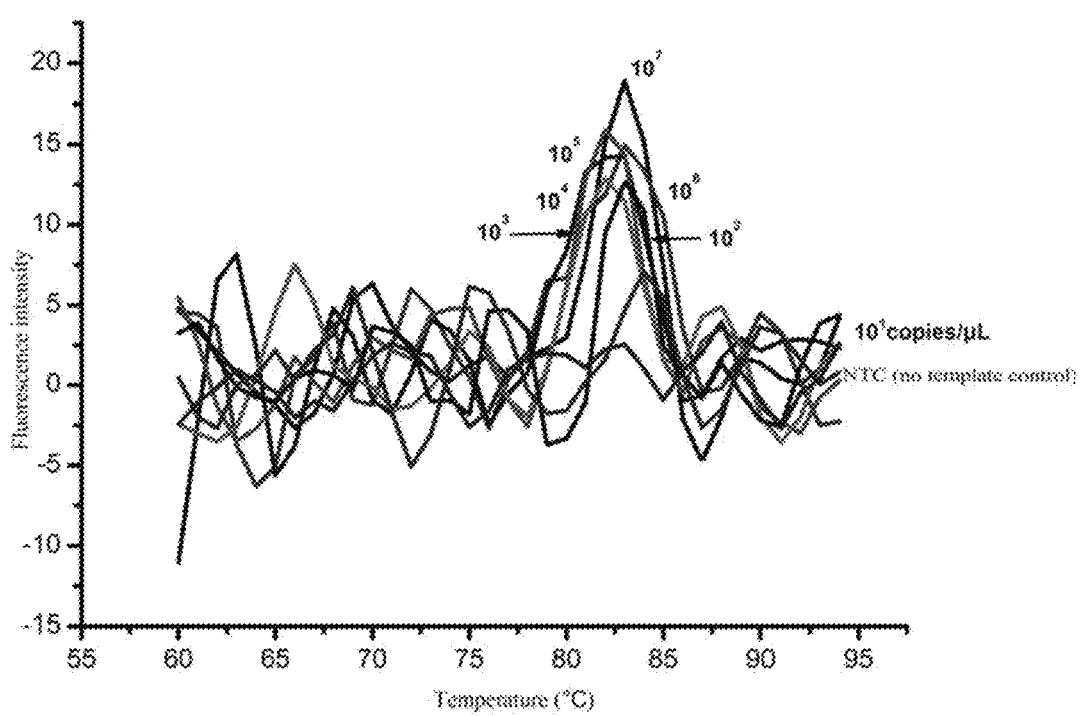
FIG. 2B is a template concentration gradient melting curve diagram while the $[Ru(bpy)_2(dppz)]^{2+}$ is served as the dye.
Figure 2C:
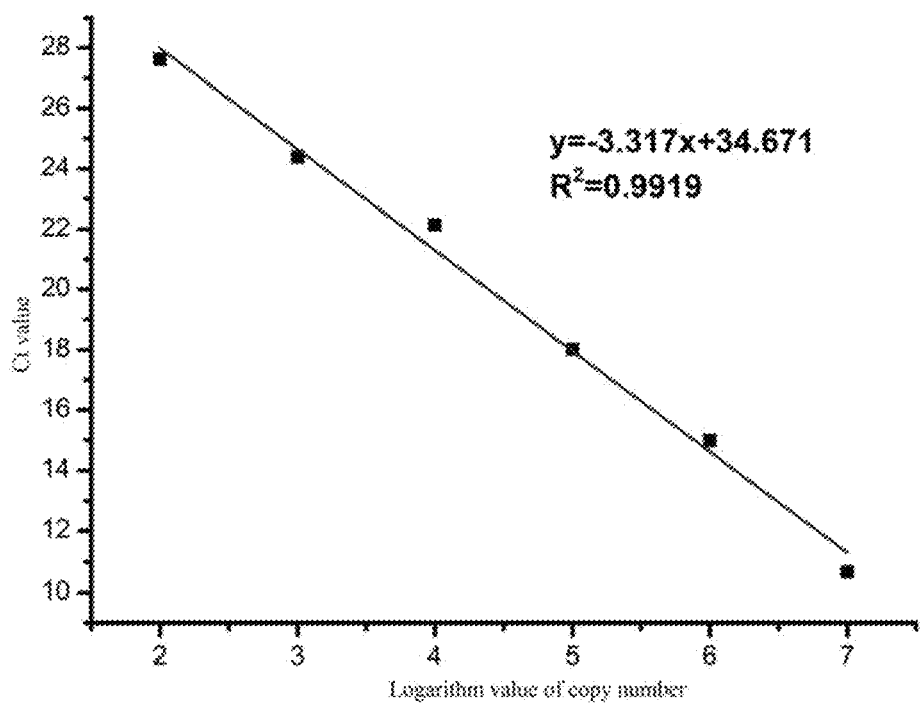
FIG. 2C is a linear fitting schematic diagram of an amount of a *Staphylococcus aureus* template and a Ct value while the $[Ru(bpy)_2(dppz)]^{2+}$ is served as the dye.

6) Experiment result:

A result is as shown in FIG. 2A, FIG. 2B and FIG. 2C, the DNA with different dilutions was used as a template, and $1\times10^2$ copies/μL of the template concentration could be detected while a real-time fluorescence quantitative PCR amplification experiment is performed, it was indicated that the detection system has higher detection sensitivity and wider dynamic range. In addition, a linearly correlation coefficient $R^2$ was greater than 0.99, it was indicated that the linearity of the real-time fluorescence quantitative PCR was better within this concentration range, a target gene could be accurately quantified. Therefore, the $[Ru(bpy)_2(dppz)]^{2+}$ had the better applicability while applied to the amplification experiment of the real-time fluorescence quantitative PCR.

(III) Linear Range and Sensitivity Analysis of Real-Time Fluorescence Quantitative PCR by Using Metal Ruthenium Complex $[Ru(Phen)_2(Dppz)]^{2+}$ 1) Bacteria culture and template DNA extraction were the same as (I).

2) Primer synthesis was the same as (I).

3) Template DNA stock solution ($1\times10^7$ copies/μL) was diluted into $1\times10^6$ copies/μL, $1\times10^5$ copies/μL, $1\times10^4$ copies/μL, $1\times10^3$ copies/μL, $1\times102$ copies/μL and $1\times101$ copies/μL in 10 times of a gradient.

4) A qPCR reaction system was the same as (I).

5) A qPCR reaction program was the same as (I).

Figure 3A:
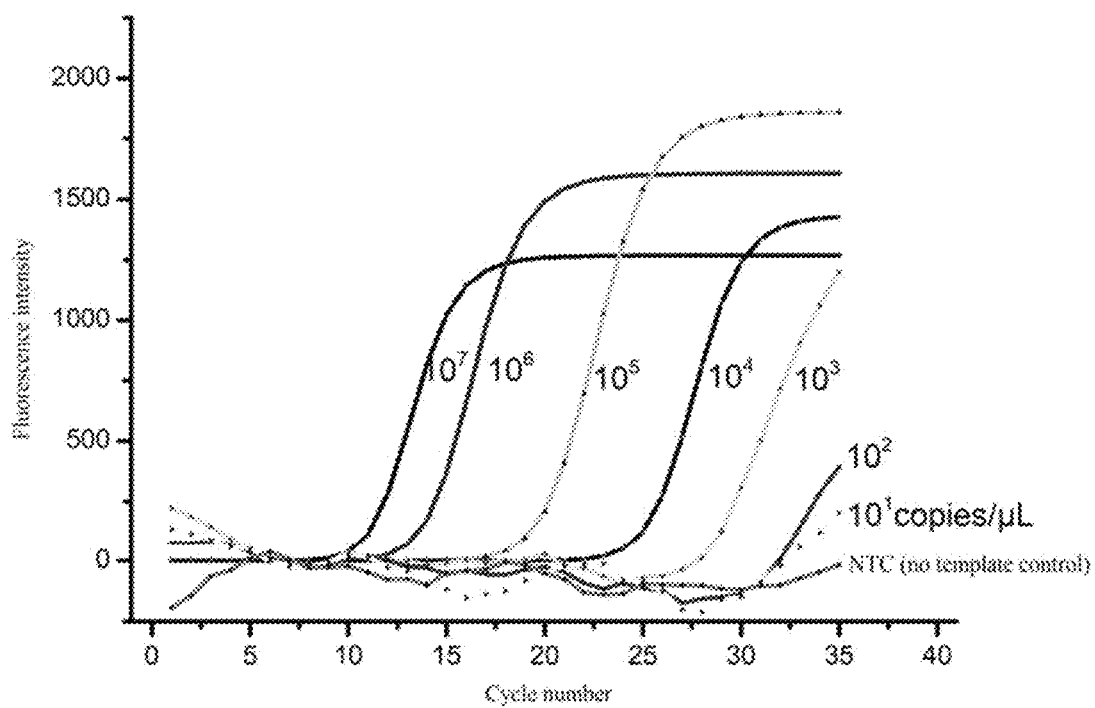
FIG. 3A is a template concentration gradient amplification curve diagram while the $[Ru(phen)_2(dppz)]^{2+}$ is served as the dye.
Figure 3B:
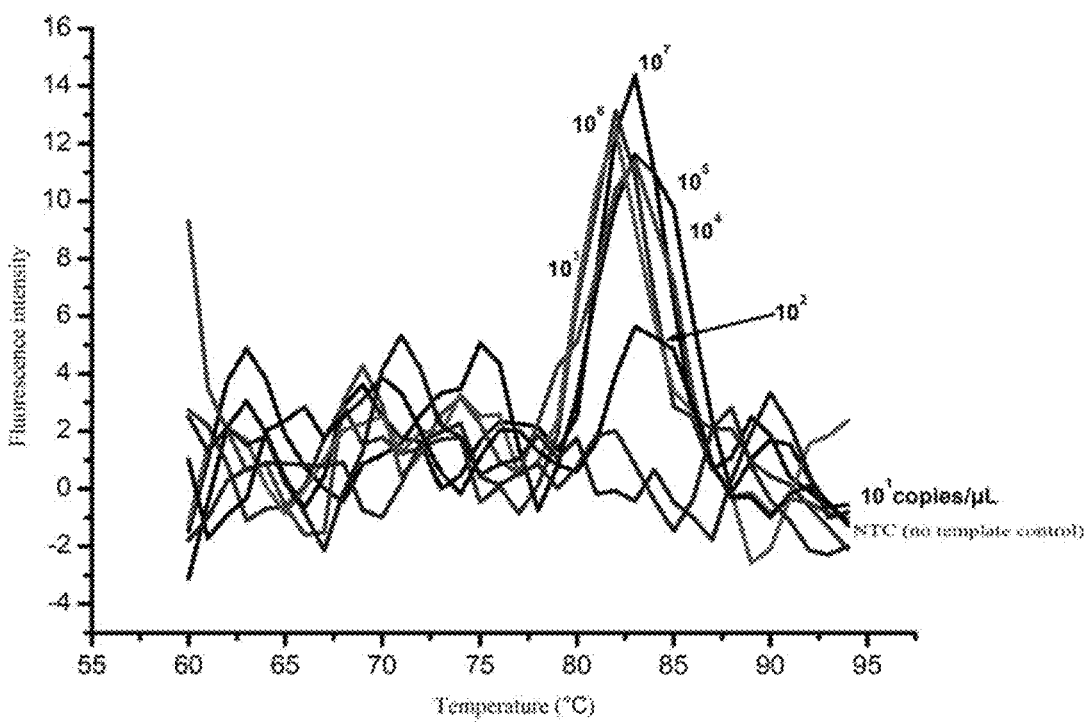
FIG. 3B is a template concentration gradient melting curve diagram while the $[Ru(phen)_2(dppz)]^{2+}$ is served a s the dye.
Figure 3C:
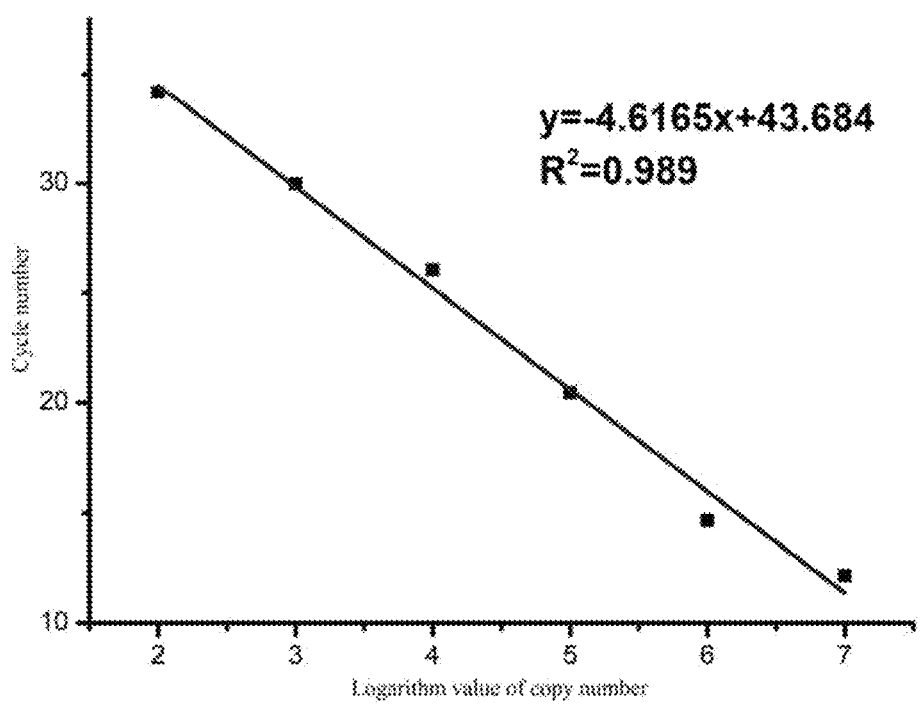
FIG. 3C is a linear fitting schematic diagram of the amount of the *Staphylococcus aureus* template and the Ct value while the $[Ru(phen)_2(dppz)]^{2+}$ is served as the dye.

6) Experiment result:

A result was as shown in FIG. 3A, FIG. 3B and FIG. 3C, the DNA with different dilutions was used as a template, and $1\times10^2$ copies/μL of the template concentration could be detected while a real-time fluorescence quantitative PCR amplification experiment was performed, it was indicated that the detection system had higher detection sensitivity and wider dynamic range. In addition, a linearly correlation coefficient $R^2$ was greater than 0.98, it was indicated that the linearity of the real-time fluorescence quantitative PCR was better within this concentration range, a target gene could be accurately quantified. Therefore, the $[Ru(phen)_2(dppz)]^{2+}$ had the better applicability while applied to the amplification experiment of the real-time fluorescence quantitative PCR.

(IV) Multiple Real-Time Fluorescence PCR Detection Based on Metal Ruthenium Complex $[Ru(Bpy)_2(Dppz)]^{2+}$ A primer used for Staphylococcus aureus was the same as (I);

A conserved sequence of an Enterobacter sakazakii Esa16S gene was used as an amplified target sequence, a design of an amplification primer was completed in November 2017, and the amplification primer was synthesized and purified by Sangon Biotech (Shanghai) Co., LtdA specific sequence is as follows:

```
pre-primer (5'-3')-2:
TCCGCAGGAGTTGAAGAGG;
and post-primer (5'-3')-2:
CAGCAGCGTGTCTGTTTCA.
```

1) Bacteria culture and template DNA extraction were the same as (I).

2) qPCR reaction system:

It was operated in a sterile environment, two groups of the pre-primer and the post-primer of Staphylococcus aureus and Enterobacter sakazakii were added at the same time, the final concentration of each primer in the reaction system was 0.2 μM, 2×Taq PCR Mastermix was 5.0 μL, 20 μM of the metal ruthenium complex $[Ru(bpy)_2(dppz)]^{2+}$ or $[Ru(phen)_2(dppz)]^{2+}$ was 1.5 μL and served as the fluorescence dye, and four groups of samples of a Staphylococcus aureus template (Staphylococcus aureus group), an Enterobacter sakazakii template (Enterobacter sakazakii group), a Staphylococcus aureus and Enterobacter sakazakii template (Staphylococcus aureus+Enterobacter sakazakii group) and NTC (blank group) were respectively set.

3) qPCR reaction program: 95° C. of initial denaturation was performed for 5 min; 95° C. of denaturation was performed for 15 s, 55° C. of annealing was performed for 15 s, 68° C. of extending was performed for 30 s and a fluorescence signal was collected, ranges of excitation and emission wavelengths of a signal channel were 400-500 nm and 550-750 nm respectively, it was 30 cycles in total; and 68° C. of the extending was performed again for 5 min. A melting curve was in 60-95° C., and the signal was measured once every 0.1° C., a temperature increasing rate was 5° C. Is.

Figure 4A:
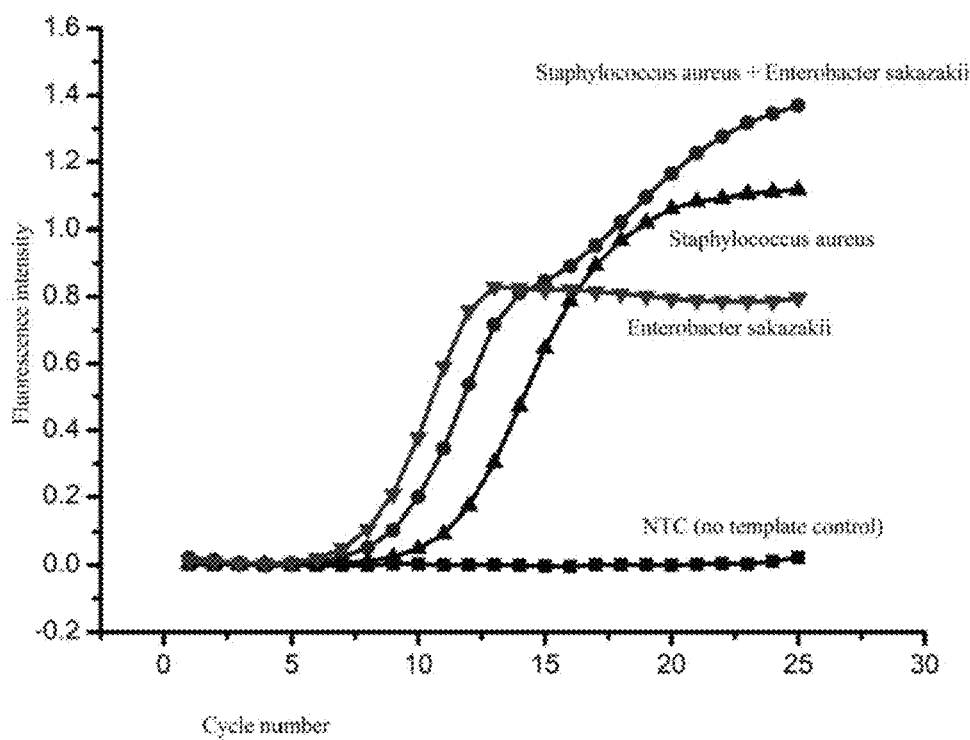
FIG. 4A is a *Staphylococcus aureus* and *Enterobacter sakazakii* real-time fluorescence double PCR detection amplification curve diagram while the $[Ru(bpy)_2(dppz)]^{2+}$ is served as the dye.
Figure 4B:
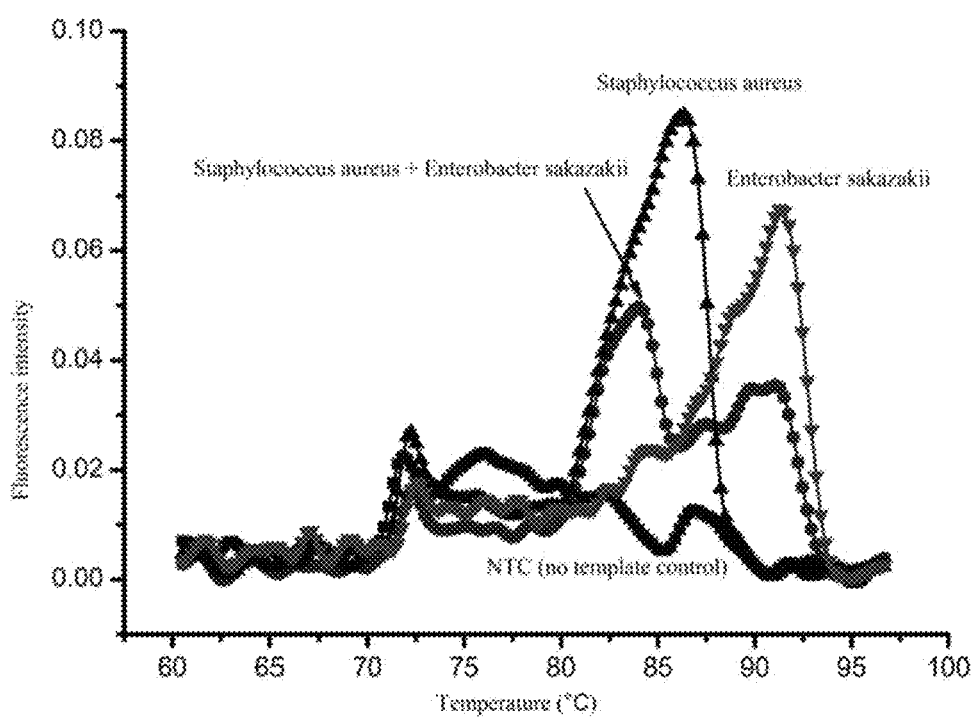
FIG. 4B is a *Staphylococcus aureus* and *Enterobacter sakazakii* real-time fluorescence double PCR detection melting curve diagram while the $[Ru(phen)_2(dppz)]^{2+}$ is served as the dye.

4) Experiment result:

As shown in FIG. 4A and FIG. 4B, after the amplification, the melting curve was analyzed, and it was discovered that: a melting curve peak of the single Staphylococcus aureus DNA appeared in about 86° C.; a melting curve peak of the amplification product of the single Enterobacter sakazakii DNA appeared in about 91° C., while the template DNAs of two types of the bacteria were added to be amplified at the same time, the amplification products thereof respectively generated one melting curve peak in 84° C. and 90° C. It was indicated from the above result that the fluorescence dye, namely the metal ruthenium complex, used in the present disclosure and the duplex real-time fluorescence PCR detection method established on the basis of this dye could accurately analyze the different DNA sequences in the system. The metal ruthenium complex could be acted as the fluorescence dye for the multiple PCR detection.

(V) Preparation of Real-Time Fluorescence Quantitative PCR Detection Kit 1.0 μL of 10×PCR buffer solution, 0.125 μL of Taq Polymerase (5U/μL), 2.0 μL of dNTP (2.5 mM), 0.375 μL of $MgCl_2$ (100 mM), 1.25 μL of KCl (1M), 0.254 of Tris-HCl (1M pH8.3) and 0.75 μL of the metal ruthenium complex dye (100 μM) were packaged together, to obtain a real-time fluorescence quantitative PCR detection kit. In use, the primers and the templates and $ddH_2O$ were added to replenish until 25 μL according to the needs of the experiment samples.

It is indicated from the above embodiment that: the metal ruthenium complex fluorescence dye used in the present disclosure is high in sensitivity, and excellent in stability, and can be applied in a real-time fluorescence quantitative PCR technology as a type of nucleic acid dye.

In conclusion, the metal ruthenium complex with the unique nucleic acid molecule "light switch" property can satisfy the requirements of the real-time PCR amplification detection, through the research on the properties thereof and the application in the real-time fluorescence quantitative PCR, it is discovered that it has the following advantages:

1) The metal ruthenium complex can maintain the stable properties under PCR high temperature and acid-base environments; (2) after the metal ruthenium complex is combined with a DNA double-strand of the qPCR amplification product, the fluorescence signal is remarkably enhanced, and in the excitation and emission wavelengths of the signal channel selected by the present disclosure, through monitoring a change of the fluorescence signal of the ruthenium complex dye in real time, a qPCR amplification curve is obtained; (3) within the wider concentration range, there is no inhibitory effect on the qPCR amplification reaction, and the high concentration of the ruthenium complex can be used, to make fluorescence reach the higher signal intensity; (4) after the qPCR amplification is completed, the melting curve can be obtained by using a real-time qPCR machine and used for distinguishing specific and non-specificamplification products; (5) under optimized experiment conditions, the detection sensitivity is comparable to the commercial dye SYBR Green I and EvaGreen; and (6) through designing an optimized primer sequence, PCR products with apparently different Tm values are generated, and the melting curve analysis can be used to achieve multiple real-time qPCR analysis, so as to achieve purposes of saving reagents and samples and improving sample throughput.

Although there is much fluorescence DNA-binding dye, not all of the fluorescence dye is suitable for the real-time qPCR, such as EB (ethidium bromide). The DNA fluorescence dye suitable for the real-time qPCR needs to meet the following conditions: (1) it is compatible with PCR amplification conditions (such as high temperature resistance and pH resistance); (2) it does not inhibit the PCR amplification reaction; and (3) it has enough high detection sensitivity, and the real-time amplification curve for quantification can be obtained. It can only be determined by experiments whether these conditions are satisfied, and cannot be speculated by theories. However, it is discovered through the experiments by the present disclosure that, the metal ruthenium complex nucleic acid molecule "light switch" is compatible with the PCR amplification experiment conditions; in addition, the amplification reaction of the PCR is not inhibited while the metal ruthenium complex is added to PCR reaction solution; and it has enough high detection sensitivity, and the conditions, such as the real-time amplification curve for the quantification, can be obtained. Therefore, the inorganic ruthenium metal complex can be served as a type of novel real-time qPCR binding dye, have the excellent properties which are not processed by the organic molecule DNA-binding dye such as SYBRGreen I and Eva Green, and have the wide application potential.

What is claimed is:

1. A real-time fluorescence quantitative PCR detection method based on a metal ruthenium complex, wherein the real-time fluorescence quantitative PCR detection method comprises the following steps:
using a metal ruthenium complex as a dye component in a real-time fluorescence quantitative PCR reaction system; using multiple nucleic acid samples with different copy numbers as standard substances, using the each standard substance as an amplification template component in the real-time fluorescence quantitative PCR reaction system respectively, and performing a real-time fluorescence quantitative PCR according to a preset reaction program, after reaction is finished respectively, drawing a standard curve according to a cycle threshold of the each standard substance; using a nucleic acid sample with an unknown copy number as an amplification template component in the real-time fluorescence quantitative PCR reaction system, performing the real-time fluorescence quantitative PCR according to the reaction program, and calculating a DNA copy number of the sample according to the standard curve and a cycle threshold of the nucleic acid sample with the unknown copy number;
wherein the metal ruthenium complex is $[Ru(phen)_2(dppz)]^{2+}$ or $[Ru(bpy)_2(dppz)]^{2+}$;
wherein a final volume of the reaction system is 10-20 μL, and a final concentration of the metal ruthenium complex in the reaction system is 3-6 μM.

2. The real-time fluorescence quantitative PCR detection method based on the metal ruthenium complex according to claim 1, wherein an extending phase of the real-time fluorescence quantitative PCR collects a fluorescence signal by using a certain channel, ranges of excitation wavelength and emission wavelength of the channel are 400-500 nm and 550-750 nm respectively, a cycle threshold of the standard substance or the nucleic acid sample with the unknown copy number is obtained according to the signal.

3. The real-time fluorescence quantitative PCR detection method based on the metal ruthenium complex according to claim 1, wherein the nucleic acid sample is a DNA or a reverse-transcribed DNA by an extracted RNA.

4. The real-time fluorescence quantitative PCR detection method based on the metal ruthenium complex according to claim 1, wherein the real-time fluorescence quantitative PCR detection method specifically comprises following steps:
1) designing a primer
according to different detection purposes and samples, selecting a target sequence and designing the primer;
2) preparing a reaction system, wherein the reaction system comprises a thermostable DNA polymerase, the primer, dNTP, a template DNA and the metal ruthenium complex;
3) real-time fluorescence quantitative PCR
according to the different target sequences and primers, setting a amplification program; using a DNA sample with a known initial concentration as a template, after performing initial denaturation on the template, circularly reacting according to the amplification program and performing fluorescence signal collection in an extending step of a circular reaction, wherein a collection channel of the fluorescence signal is: 400-500 nm of an excitation wavelength, and 550-750 nm of an emission wavelength; after the circular reaction is over, performing the extending again; and then according to the collected signal, establishing an amplification curve, and determining a cycle threshold of the DNA sample by the amplification curve;
4) repeating the step 3), to obtain the cycle threshold of each DNA sample with the different initial concentrations, and establishing a standard curve in combination with the concentration of the corresponding DNA sample; and
5) according to the step 3), amplifying a DNA sample with an unknown initial concentration, to obtain a corresponding cycle threshold and substituted into the standard curve obtained in the step 4), thereby acquiring an initial concentration of the DNA sample by calculating.

5. The real-time fluorescence quantitative PCR detection method based on the metal ruthenium complex according to claim 4, wherein the amplification program is: performing heat-denaturation on the template after the initial denaturation, and renaturing a primer with a single-strand template obtained by thermal denaturation, then extending under the effect of a DNA polymerase.

6. The real-time fluorescence quantitative PCR detection method based on the metal ruthenium complex according to claim 4, wherein the DNA sample with the unknown initial concentration is obtained by extraction and purification through a kit.

7. A real-time fluorescence quantitative PCR detection kit based on a metal ruthenium complex, wherein the kit comprises a metal ruthenium complex served as nucleic acid dye in a real-time fluorescene quantitative PCR reaction system,
wherein the metal ruthenium complex is $[Ru(phen)_2(dppz)]^{2+}$ or $[Ru(bpy)_2(dppz)]^{2+}$;
wherein a final volume of the reaction system is 10-20 μL, and a final concentration of the metal ruthenium complex in the reaction system is 3-6 μM.

8. A real-time fluorescence quantitative PCR detection system based on a metal ruthenium complex, wherein comprising a kit and a qPCR meter for preparing a real-time fluorescence quantitative PCR reaction system, the kit comprises a metal ruthenium complex served as nucleic acid dye in a real-time fluorescence quantitative PCR reaction system, while the qPCR machine meter performs fluorescence signal collection in an extending step of a circular reaction, a used collection channel of a fluorescence signal is as follows: an excitation wavelength is 400-500 nm, and an emission wavelength is 550-750 nm,
wherein the metal ruthenium complex is $[Ru(phen)_2(dppz)]^{2+}$ or $[Ru(bpy)_2(dppz)]^{2+}$;
wherein a final volume of the reaction system is 10-20 μL, and a final concentration of the metal ruthenium complex in the reaction system is 3-6 μM.

* * * * *